(12) United States Patent
Norrant et al.

(10) Patent No.: US 11,865,252 B2
(45) Date of Patent: Jan. 9, 2024

(54) ASSEMBLY FOR DISPENSING A FLUID PRODUCT

(71) Applicant: APTAR FRANCE SAS, Le Neubourg (FR)

(72) Inventors: Matthieu Norrant, Houlbec Cocherel (FR); Maxime Huppé, Caudebec les Elbeuf (FR)

(73) Assignee: APTAR FRANCE SAS, Le Neubourg (FR)

( * ) Notice: Subject to any disclaimer, the term of this patent is extended or adjusted under 35 U.S.C. 154(b) by 825 days.

(21) Appl. No.: 16/968,010

(22) PCT Filed: Feb. 4, 2019

(86) PCT No.: PCT/FR2019/050239
§ 371 (c)(1),
(2) Date: Aug. 6, 2020

(87) PCT Pub. No.: WO2019/155150
PCT Pub. Date: Aug. 15, 2019

(65) Prior Publication Data
US 2021/0369992 A1 Dec. 2, 2021

(30) Foreign Application Priority Data
Feb. 7, 2018 (FR) .................................. 1851001

(51) Int. Cl.
*A61M 15/08* (2006.01)
*H04N 23/53* (2023.01)
*G16H 40/67* (2018.01)
*G16H 20/10* (2018.01)

(52) U.S. Cl.
CPC ............ *A61M 15/08* (2013.01); *H04N 23/53* (2023.01); *A61M 2205/215* (2013.01);
(Continued)

(58) Field of Classification Search
CPC ............ A61M 15/08; A61M 2205/215; A61M 2205/3561; A61M 2205/3584;
(Continued)

(56) References Cited

U.S. PATENT DOCUMENTS

| 2013/0063579 A1 | 3/2013 | Hanina et al. |
| 2018/0085540 A1* | 3/2018 | Dantsker ................ G16H 20/13 |
| 2018/0092595 A1* | 4/2018 | Chen .................... A61B 5/1123 |

FOREIGN PATENT DOCUMENTS

| FR | 3 024 655 A1 | 2/2016 |
| WO | 02/085282 A1 | 10/2002 |

(Continued)

OTHER PUBLICATIONS

International Search Report for PCT/FR2019/050239 dated May 22, 2019 [PCT/ISA/210].
(Continued)

*Primary Examiner* — Kendra D Carter
*Assistant Examiner* — Arielle Wolff
(74) *Attorney, Agent, or Firm* — Sughrue Mion, PLLC

(57) ABSTRACT

A fluid dispenser assembly having a nasal fluid dispenser device (1000) with a reservoir (30) and, a dispenser head (1) assembled on the reservoir (30); a remote mobile device (2000); and an orientation sensor (113) to obtain optimal orientation of the dispenser device (1000) when actuated. The sensor determines the three-dimensional orientation of the device, including the angle (α) of the device relative to said remote mobile device. A second sensor (121) is provided for detecting when the device (1000) is actuated by the user. The remote mobile device includes an accelerometer to determine its position in three-dimensional space, in particular the angle (β) of the remote mobile device (2000) relative to the vertical.

15 Claims, 3 Drawing Sheets

(52) U.S. Cl.
CPC ............... *A61M 2205/3561* (2013.01); *A61M 2205/3584* (2013.01); *A61M 2205/502* (2013.01); *A61M 2205/581* (2013.01); *A61M 2205/582* (2013.01); *A61M 2205/583* (2013.01); *A61M 2210/0618* (2013.01); *G16H 20/10* (2018.01); *G16H 40/67* (2018.01)

(58) Field of Classification Search
CPC ...... A61M 2205/502; A61M 2205/581; A61M 2205/582; A61M 2205/583; A61M 2210/0618; A61M 2205/073; A61M 2205/332; A61M 2205/3592; A61M 2230/62; A61M 11/02; H04N 23/53; G16H 20/10; G16H 40/67; G16H 20/13; B05B 11/062; B05B 11/1053
See application file for complete search history.

(56) References Cited

FOREIGN PATENT DOCUMENTS

| | | |
|---|---|---|
| WO | 2016/048435 A1 | 3/2016 |
| WO | 2016/075525 A1 | 5/2016 |
| WO | 2017/220879 A1 | 12/2017 |

OTHER PUBLICATIONS

Written Opinion for PCT/FR2019/050239 dated May 22, 2019 [PCT/ISA/210].

International Preliminary Report on Patentability dated Aug. 11, 2020, from the International Bureau in International Application No. PCT/FR2019/050239.

* cited by examiner

ASSEMBLY FOR DISPENSING A FLUID PRODUCT

CROSS REFERENCE TO RELATED APPLICATIONS

This application is a National Stage of International Application No. PCT/FR2019/050239 filed Feb. 4, 2019, claiming priority based on French Patent Application No. 1851001 filed Feb. 7, 2018.

The present invention relates to a fluid dispenser assembly comprising a nasal fluid dispenser device and a remote mobile device, such as a smartphone.

Nasal dispenser devices are well known. They generally comprise a reservoir containing one or more doses of fluid, and a dispenser head that is movable relative to said reservoir so as to dispense the fluid, in particular via a pump, a metering valve, or a piston that slides in said reservoir. When the user wishes to use the device, the user inserts the dispenser head into the nostril and actuates the device so as to dispense a dose of fluid, generally in the form of spray.

A drawback with prior-art devices relates to the effectiveness of the dose that is dispensed in the nostril, in particular when the purpose of the dispensed fluid is to act on the brain. Specifically, only a tiny portion of the dose generally reaches the target zone for this type of treatment, namely the olfactory zone including the ethmoid sinuses, in particular because of the orientation of the administering device in the nostril, which varies from one patient to another. Unfortunately, it appears that this orientation determines whether targeting of the target zone is successful, in particular for a compact spray that is used to obtain the maximum deposition in the target zone.

Document WO 98/57690 describes a nasal dispenser device including orientation means pressing on the user's top lip. Although that improves the quality of insertion, such an orientation device does not make it possible to guarantee optimal orientation when the dose is dispensed.

Documents WO 02/085282 and FR 3 024 655 describe other prior-art devices.

An object of the present invention is to provide a dispenser assembly that does not have the above-mentioned drawbacks.

In particular, an object of the present invention is to provide a nasal dispenser assembly that makes it possible to control the orientation of the device in the nostril, whatever the morphology of the patient and whatever the patient's standing, lying, or reclining position when the device is used.

Another object of the present invention is to provide a nasal dispenser assembly that improves the percentage of active fluid that is deposited on the olfactory zone and/or on the ethmoid sinuses.

Another object of the present invention is to provide a nasal dispenser assembly that makes it possible to inform the user in real time about the quality of insertion of the device in the nostril.

Another object of the present invention is to provide a nasal dispenser assembly that enables the user to correct the orientation of the device in the nostril when it is actuated.

Another object of the present invention is to provide a nasal dispenser assembly that is simple and inexpensive to manufacture and to assemble.

The present invention thus provides a fluid dispenser assembly, comprising:
 a nasal fluid dispenser device, said device comprising a reservoir containing fluid, a dispenser head being assembled on said reservoir, said dispenser head being provided with a dispenser orifice; and
 a remote mobile device, such as a smartphone;
 wherein said dispenser device includes at least one orientation sensor and communicates with said remote mobile device in order to assist and guide the user in real time, so as to obtain optimal orientation of the dispenser device when said device is actuated;
 wherein said orientation sensor, such as an accelerometer or a gyro, determines in real time the three-dimensional orientation of said device, in particular the angle $\alpha$ of said device relative to said remote mobile device;
 wherein said device includes a second sensor, such as an accelerometer, for detecting when the device is actuated by the user; and
 wherein said remote mobile device includes an accelerometer that makes it possible to determine its position in three-dimensional space, in particular the angle $\beta$ of said remote mobile device relative to the vertical.

Advantageously, said device includes a top support and a bottom support that are arranged around said dispenser head.

Advantageously, said top support is arranged above a finger rest of said dispenser head, and said bottom support is arranged around a skirt of said dispenser head.

Advantageously, said device further includes a wireless communication module, advantageously a Bluetooth® module, for communicating with said remote mobile device, and for relaying in real time the position of said device relative to the user's nostril.

Advantageously, said device includes an electronic module, such as a printed circuit, including a microprocessor containing software for processing information provided by the sensor(s).

Advantageously, said device includes at least one visual and/or audible and/or tactile indicator device for transmitting information in real time to the user.

Advantageously, said device includes a screen that is adapted to display information that can be seen by the user.

Advantageously, said device includes a loudspeaker and/or a vibrator element for providing the user with audible and/or tactile information.

Advantageously, said remote mobile device includes a screen and a camera.

Advantageously, said reservoir contains a single dose or only two doses of fluid.

These and other characteristics and advantages appear more clearly from the following detailed description, given by way of non-limiting example, and with reference to the accompanying drawings, in which.

Figure 1:
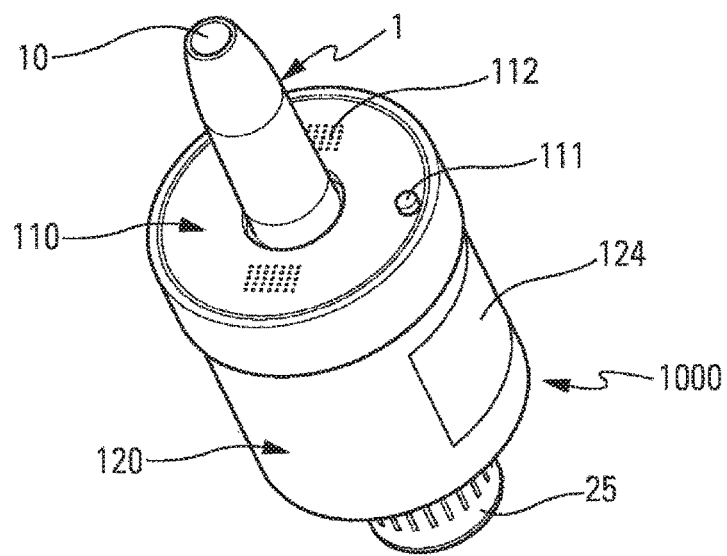
FIG. 1 is a diagrammatic perspective view of a nasal dispenser device in an advantageous embodiment.

The present invention relates more particularly to a single-dose device, as disclosed in document WO 02/45866. However, it should be understood that the present invention is not limited to that type of device, but, on the contrary, applies to any fluid or powder dispenser device either of the single-dose type, i.e. including a reservoir that contains a single dose that is dispensed in a single actuation, of the two-dose type, i.e. including a reservoir that contains two doses that are dispensed in two successive actuations, or else of the multi-dose type, i.e. including a reservoir that contains more than two doses.

In the description below, the terms "top", "bottom", "upwards", "downwards", "horizontal", and "vertical" are relative to the upright position of the device shown in FIGS. 2, 3, and 11 to 13. The terms "axial" and "radial" are relative to the longitudinal central axis X of the device, shown in FIG. 2.

The device 1000 given by way of example is a single-dose device that comprises a reservoir 30 including an air inlet 31 and a fluid outlet 32, and containing a single dose of fluid which may be liquid or powder. The air inlet 31 of the reservoir is connected to an air expeller 20, and the fluid outlet 32 of the reservoir is connected to a dispenser orifice 10 of the device. The fluid outlet 32 is closed by a closure element 50 that is force fitted in said fluid outlet 32. The air inlet 31 is provided with a fluid retainer member 40 that is suitable for retaining the fluid in the reservoir 30 before the device is actuated. The air expeller 20 is actuated manually by the user, and is suitable for creating a flow of air that passes through the reservoir 30 so as to deliver the fluid that it contains towards the dispenser outlet 10.

The reservoir 30 is secured, in particular as a tight fit, in a dispenser head 1 that includes the dispenser orifice 10. Advantageously, the dispenser head 1 includes a finger rest 2 that extends radially so as to facilitate actuation. A hollow sleeve 3, forming a nasal endpiece, extends axially upwards from said finger rest 2, and is terminated at said dispenser outlet 10. Preferably, the hollow sleeve 3 is of small radial dimension, so as to be suitable for inserting in a nostril at the time of actuation. On the opposite side of the finger rest 2, the dispenser head 1 includes a skirt 5 that extends axially downwards from said finger rest 2. Optionally, a hollow tube 6 may be arranged radially outside said skirt 5, as can be seen in FIGS. 2 and 3.

The device 1000 includes a mechanical opening system 61, 62 that is preferably secured to the air expeller 20, i.e. it is actuated simultaneously with said air expeller 20 being actuated, and that is suitable for co-operating with said closure element 50 so as to expel it mechanically from its closed position while the device is being actuated. In the embodiment shown in the figures, the mechanical opening system includes a set of rods 61, 62, having a first rod portion 61 that is secured to the air expeller 20, and a second rod portion 62 that is thrust by said first rod portion 61 when the device is actuated. At the end of their actuation stroke, i.e. in the dispensing position, the set of rods 61, 62 co-operate with the closure element 50 so as to expel it mechanically from its closed position.

The fluid retainer member 40 may advantageously be made integrally with the second rod portion 62. Thus, the fluid retainer member 40 can be made in leaktight and airtight manner before the device is actuated, the air pressure created by the air expeller 20 penetrating into the reservoir 30 only when said retainer member 40 is moved together with the second rod portion 62, by being thrust by the first rod portion 61.

Figure 2:
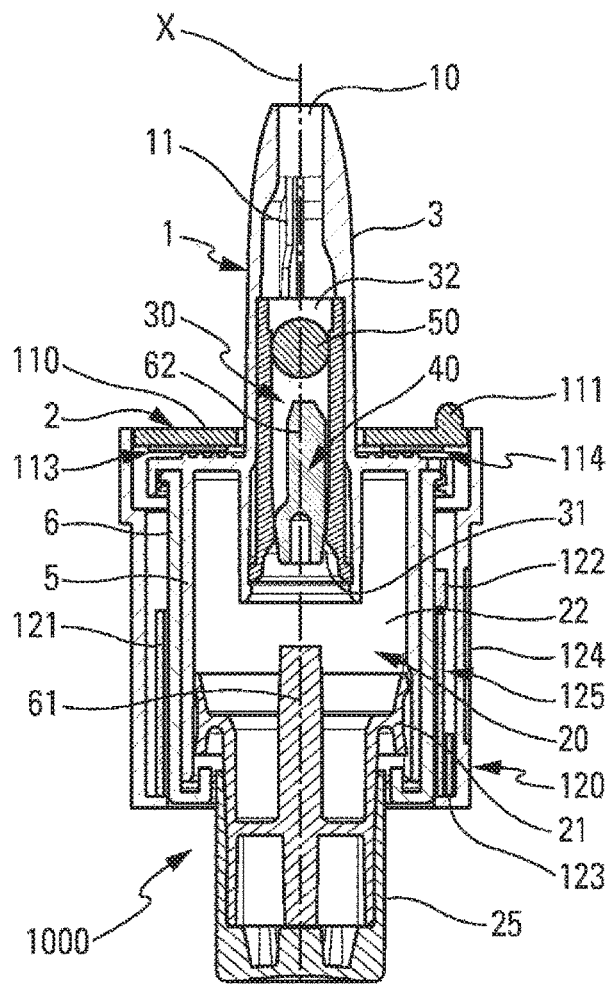
FIGS. 2 and 3 are diagrammatic views of the FIG. 1 device in its rest position, shown in section respectively in two different section planes.
Figure 3:
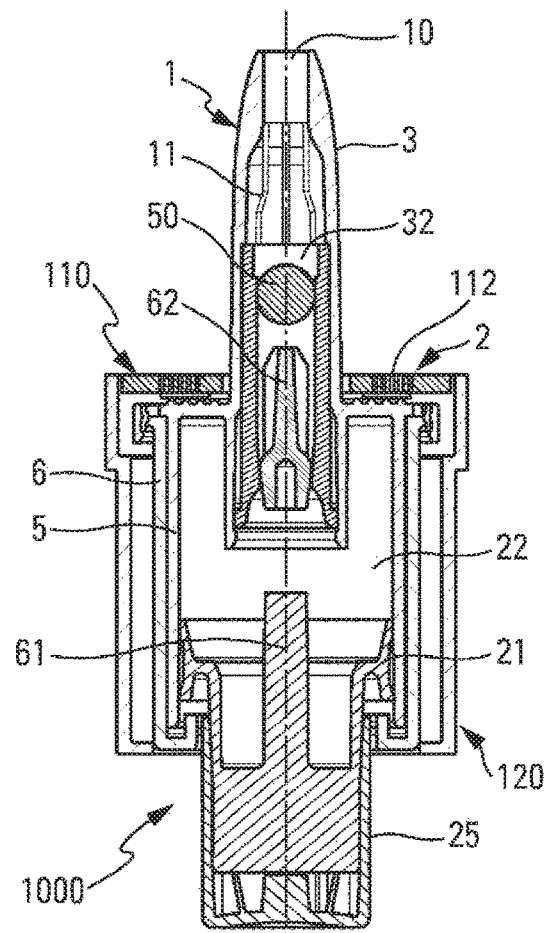

The closure element 50 may be spherical, e.g. a ball, in particular made of plastics material, as shown in FIGS. 2 and 3.

The air expeller 20, as shown in FIGS. 2 and 3, comprises a piston 21 that slides in an air chamber 22, the piston 21 being actuated manually by the user. The air chamber 22 may be formed by said skirt 5 of the head.

Advantageously, actuation of the device 1000 is performed by means of a pusher element 25 that is assembled on said piston 21.

The piston 21 is secured to the first rod portion 61, advantageously being formed integrally therewith.

When it is desired to actuate the device 1000, the user firstly places fingers on the finger rest 2 of the dispenser head 1, and secondly a thumb on the pusher element 25, and exerts an axial actuation force that moves the first rod portion 61 and the piston 21 towards the dispensing position. The piston 21 of the air expeller co-operates in airtight manner with the air chamber 22, such that the air contained in said air chamber 22 is compressed progressively during actuation.

After an initial actuation stroke for compressing air, the top axial end of the first rod portion 61 comes into contact with the retainer member 40 and thus with the second rod portion 62.

Continued actuation moves said retainer member 40 axially upwards inside the reservoir 30, thus away from its position of sealed shutting or closing of the air inlet 32. At that moment, the compressed air in the air chamber 22 can thus penetrate into the reservoir 30. At the same moment, the top axial end of the second rod portion 62 comes into contact with the closure element 50.

Continued actuation thus moves the closure element 50 axially upwards, away from its closed position.

When the sealing of the closure element 50 is broken, said closure element is expelled out from the reservoir 30 so as to enable the fluid or powder to be dispensed under the effect of the compressed air. The closure element 50 thus becomes jammed in splines 11 of the dispenser head 1, which splines prevent in particular any risk of said closure element 50 being expelled out from said dispenser head 1.

Naturally, the present invention is not limited to the single-dose device described above, but applies to any nasal device, whether it be a single-dose device, a two-dose device, or a multi-dose device.

In the invention, the nasal device 1000 includes at least one orientation sensor and communicates with a remote mobile device 2000, in particular via a dedicated application, in order to assist and guide the user in real time, so as to obtain optimal orientation of the dispenser device when it is actuated.

An object is to ensure optimal positioning of the device given the morphology of the patient, with this applying at the same moment as the device is actuated. This enables better deposition of the medication in the nostril.

The user may optionally run a test beforehand at a health specialist's premises in order to know the optimal angle for that user's own morphology, thereby enabling the user to configure the associated application.

Preferably, the device 1000 includes a top support 110 and a bottom support 120 that are arranged around the dispenser head 1, said top and bottom supports incorporating the elements of the invention. In this way, neither the operation nor the performance of the fluid dispenser device are modified by the present invention. In particular, the top support 110 may be arranged above the finger rest 2 of the head 1, and the bottom support 120 may be arranged around the skirt 5 of the head 1 or around said hollow tube 6.

In the invention, the device 1000 includes an orientation sensor 113, such as an accelerometer or a gyro, in order to know the three-dimensional orientation of the device in real time, in particular its angular position relative to the remote mobile device.

The device 1000 includes a second sensor 121, such as an accelerometer, for detecting when the dose is triggered by the user. The second sensor may be calibrated precisely so that only the acceleration generated by the actuation of the device is detected.

The remote mobile device 2000 includes an accelerometer that makes it possible to determine its position in three-dimensional space, in particular its angle β relative to the vertical.

In the initial position of the patient (standing, seated, reclining at ±45°, or lying), software calculates the optimal angles.

The device 1000 further includes a wireless communication module 123, advantageously a Bluetooth® module, for communicating with a remote mobile device 2000, such as a smartphone or a tablet, and for relaying in real time the position of the device relative to the user's nostril.

The device 1000 also includes an electronic module 125, such as a printed circuit or printed circuit board (PCB), including a microprocessor containing the software for processing information provided by the sensor(s).

Advantageously, the device 1000 also includes at least one visual and/or audible and/or tactile indicator device for transmitting information to the user. Thus, the device may include a screen 124 that is adapted to display information that can be seen by the user, and/or a light-emitting diode 111. It may also include a loudspeaker 112 and/or a vibrator element 122 for providing the user with audible and/or tactile information, which can be useful for the visually impaired, for example.

The operation of the assembly is described below with reference to FIGS. 4 to 13. In this embodiment, the remote mobile device 2000 is a smartphone.

Figure 4:
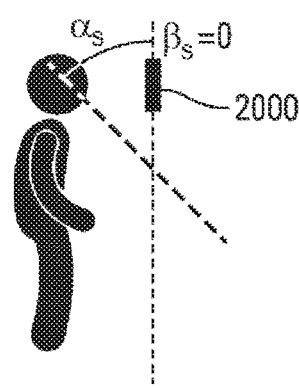
FIGS. 4 to 6 are diagrammatic views of a user, shown respectively in standing, lying, and reclining positions.
Figure 5:
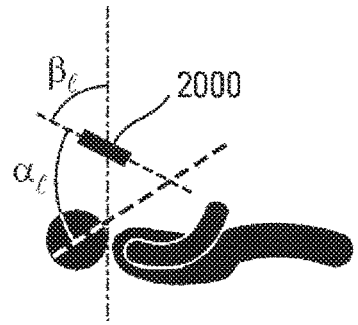
Figure 6:
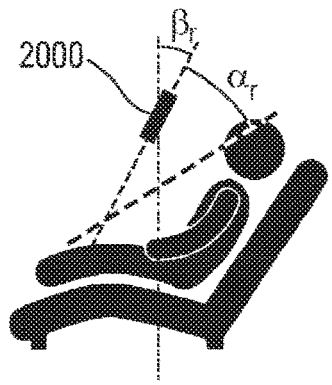

As can be seen in FIGS. 4 to 6, whatever the position of the user, standing (s) as in FIG. 4, lying (l) as in FIG. 5, or reclining (r) as in FIG. 6, the user's face faces the screen 2001 of the smartphone, so as to have the plane of the screen parallel to the plane of the face. Advantageously, the front camera 2002 of the smartphone can be used to ensure that the user is looking straight at the screen.

$\alpha_s$, $\alpha_l$, $\alpha_r$: the angles of the nasal device relative to the smartphone are always identical whatever the position of the user.

$\beta_s$, $\beta_l$, $\beta_r$: the angles of the smartphone relative to the vertical are determined by the accelerometer of the smartphone; this measurement makes it possible to determine the position of the user, and thus to display the real position of the device on the screen of the smartphone.

Description of the Operating Steps:

Rest position: the accelerometer of the device does not indicate any movement; the electronics of the device are on standby; the application indicates that the device is not in the patient's hand.

Figure 7:
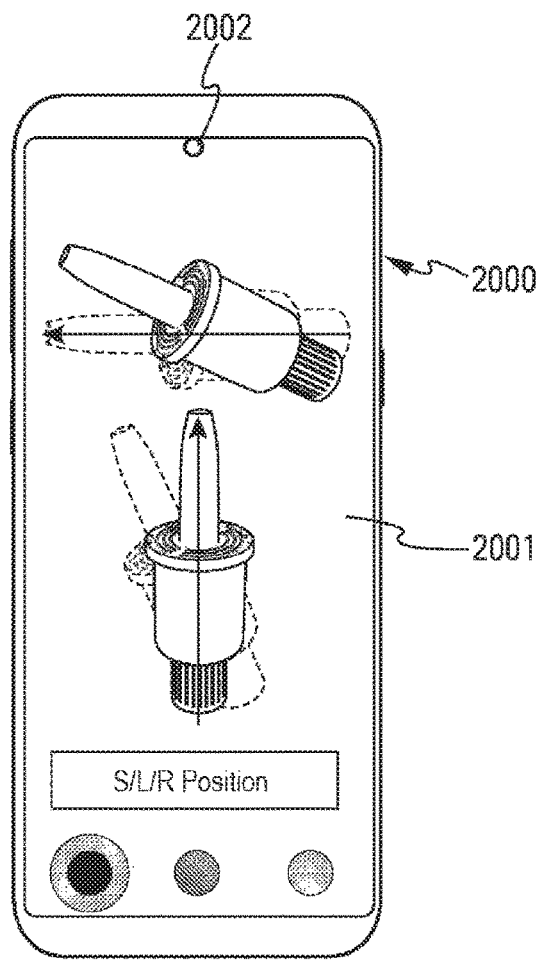
FIG. 7 is a diagrammatic view of a screen, in particular a smartphone screen, while the user is using the device, informing the user in real time about the orientation of the device in the nostril.
Figure 9:
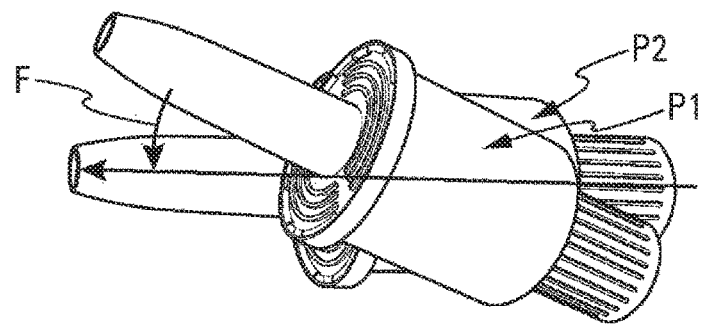
FIGS. 9 and 10 are detail views showing the device as displayed on the screen of FIG. 7, for showing the user how to improve the orientation of the device in the nostril before actuation.
Figure 10:
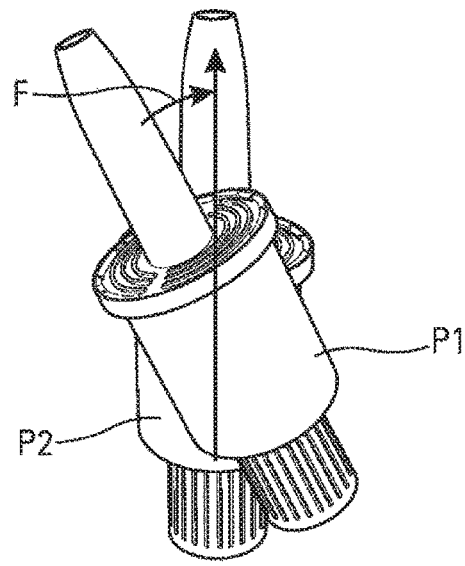

First hand-held position: the accelerometer of the device detects the movement of the device; the electronics of the device are activated; the combination of the measurements of the angles α and β makes it possible to determine the position of the user and the position of the device relative to said user; if the positioning is outside the optimal zone, as shown in FIG. 7, an indication, such as a red spot, is displayed on the screen of the smartphone; simultaneously, the screen displays the real position P1 of the device in three dimensional space and the optimal position P2, and one or more arrows F can guide the user so as to improve the position of the device towards the optimal position P2, as shown in FIGS. 9 and 10; simultaneously, audible instructions can be issued, such as "slope the device upwards/downwards" and/or "turn the device towards your left/right", for example; when the user approaches the optimal orientation, a different indication, such as an orange spot, can be displayed on the screen of the smartphone.

Figure 8:
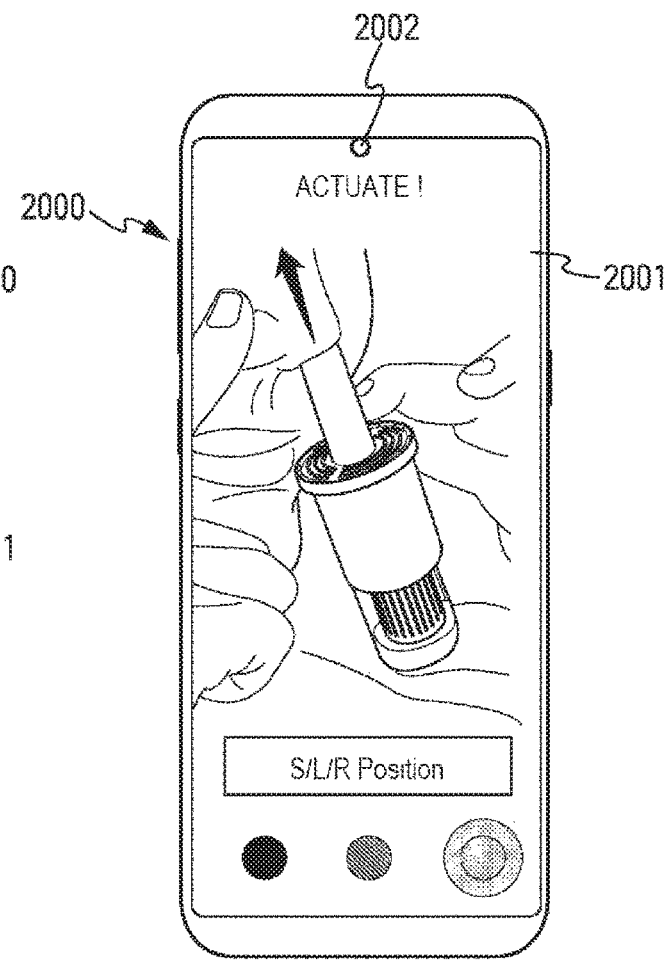
FIG. 8 is a view similar to the view in FIG. 7, telling the user that the device can be actuated.

Optimal position: when the user has positioned the device in the optimal position, as shown in FIG. 8, a different indication, such as a green spot, can be displayed on the screen of the smartphone, and the user can actuate the device so as to dispense the dose; simultaneously, the screen of the smartphone can display a message telling the user to actuate the device, such as the word "actuate" and/or an animated arrow indicating that it is necessary to trigger the dose, for example; in addition, an audible instruction can be issued, such as "actuate the device" and/or "trigger the dose", for example.

If during actuation the device moves away from the optimal zone, visual or audible messages can be issued, such as "dose not optimal" or "risk of insufficient dose", for example.

Figure 11:
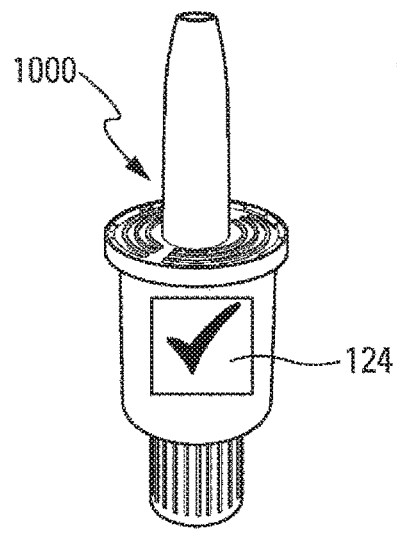
FIGS. 11 to 13 are diagrammatic perspective views of the FIG. 1 device after actuation, with a screen of the device displaying the dose dispensing status, respectively good, medium, and bad.
Figure 12:
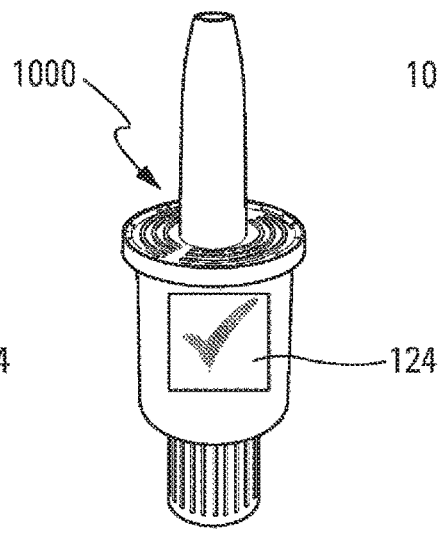
Figure 13:
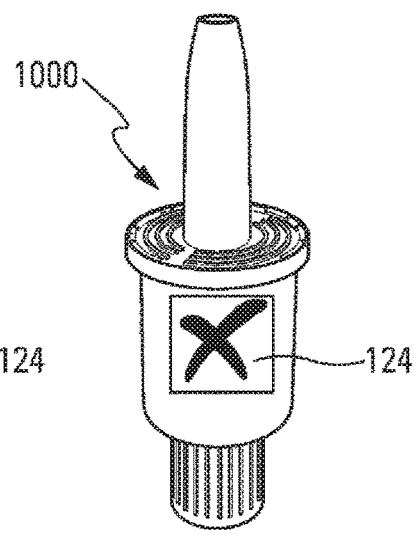

After actuation, the screen 2001 of the smartphone 2000, and optionally also the screen 124 of the device 1000, if one is provided, can display the status of the dose that has been dispensed, as a function of the position of the device at the precise moment of dispensing, such as "Dose correct", "Dose not optimal", or "Risk of insufficient dose", for example. FIGS. 11 to 13 show possible displays on the screen 124 of the device 1000.

The present invention thus provides numerous advantages:

it promotes precise angular positioning when a dose is dispensed, thereby ensuring optimal deposition of the fluid that is dispensed in the nostril;

it provides orientation assistance "in real time", in particular together with the safety feature of confirming the optimal position before actuation;

it provides a solution that is usable with a large number of nasal dispenser devices of the same type, and is thus not limited to the embodiment described;

it has a minor impact on the design and bulkiness of the device, and as a result remains easy to carry;

it does not have any impact on the operation and performance of the device, and thus does not modify the performance of the fluid that is dispensed;

it makes it possible to administer the fluid easily to a third party;

it enables use in any position, in particular standing, sitting, lying;

it makes it possible to transfer data to doctors, health specialists, pharmacists, regulatory authorities, insurers; and it trains the user: finding the optimal angle becomes easier and easier for the user, who subconsciously memorizes the proper position of the device relative to the user's own morphology.

The present invention is described above with reference to several embodiments, but naturally any modification could be applied thereto by a person skilled in the art, without going beyond the ambit of the present invention, as defined by the accompanying claims.

The invention claimed is:

1. A fluid dispenser assembly, characterized in that it comprises:
 a nasal fluid dispenser device, said device comprising a reservoir containing fluid, a dispenser head being assembled on said reservoir, said dispenser head being provided with a dispenser orifice; and
 a remote mobile device;
 wherein said dispenser device includes at least one orientation sensor and communicates with said remote mobile device in order to assist and guide a user in real time, so as to obtain optimal orientation of the dispenser device when said device is actuated;
 wherein said orientation sensor determines in real time a three-dimensional orientation of said device, wherein the three-dimensional orientation is determined by an angle ($\alpha$) of said device relative to said remote mobile device;
 wherein said device includes a second sensor for detecting when the device is actuated by the user; and
 wherein said remote mobile device includes an accelerometer that determines the mobile devices position in three-dimensional space, wherein the position in three-dimensional space is determined by an angle ($\beta$) of said remote mobile device relative to a vertical orientation.

2. An assembly according to claim 1, wherein said device further includes a top support and a bottom support that are arranged around said dispenser head.

3. An assembly according to claim 2, wherein said top support is arranged above a finger rest of said dispenser head, and said bottom support is arranged around a skirt of said dispenser head.

4. An assembly according to claim 1, wherein said device further includes a wireless communication module for communicating with said remote mobile device, and for relaying in real time a position of said device relative to the user's nostril.

5. An assembly according to claim 4, wherein the wireless communication module comprises a Bluetooth module.

6. An assembly according to claim 1, wherein said device further includes an electronic module including a microprocessor containing software for processing information provided by the sensor(s).

7. An assembly according to claim 6, wherein the electronic module comprises a printed circuit.

8. An assembly according to claim 1, wherein said device further includes at least one visual and/or audible and/or tactile indicator device for transmitting information in real time to the user.

9. An assembly according to claim 8, wherein said visual indicator device is a screen that is adapted to display information that can be seen by the user.

10. An assembly according to claim 8, wherein said audible indicator device is a loudspeaker and/or tactile indicator device is a vibrator element for providing the user with audible and/or tactile information.

11. An assembly according to claim 1, wherein said remote mobile device further includes a screen and a camera.

12. An assembly according to claim 1, wherein said reservoir contains a single dose or only two doses of fluid.

13. An assembly according to claim 1, wherein the remote mobile device comprises a smartphone.

14. An assembly according to claim 1, wherein the orientation sensor comprises an accelerometer or a gyro.

15. An assembly according to claim 1, wherein the second sensor comprises an accelerometer.

* * * * *